United States Patent [19]

Adam

[11] Patent Number: 5,486,608
[45] Date of Patent: Jan. 23, 1996

[54] CATIONIC COMPOUNDS, THEIR PREPARATION AND THE USE THEREOF FOR THE PHOTOCHEMICAL STABILISATION OF BASIC DYEABLE POLYAMIDE FIBRE MATERIALS

[75] Inventor: Jean-Marie Adam, Rosenau, France

[73] Assignee: Chiba-Geigy Corporation, Tarrytown, N.Y.

[21] Appl. No.: 168,012

[22] Filed: Dec. 15, 1993

[30] Foreign Application Priority Data

Dec. 17, 1992 [CH] Switzerland ................ 3850/92

[51] Int. Cl.$^6$ ................................ C07D 295/037
[52] U.S. Cl. .................... 544/108; 544/113; 544/143; 544/180; 544/216; 548/257
[58] Field of Search ................... 544/108, 143, 544/180, 216; 546/176, 271, 273; 548/257

[56] References Cited

U.S. PATENT DOCUMENTS 5,037,979  8/1991  Höhener .................... 544/216

FOREIGN PATENT DOCUMENTS 0357545  3/1990  European Pat. Off. .
1559131  3/1969  France .

OTHER PUBLICATIONS

Eur. Polymer J., (1981), vol. 17 #10 pp. 1041–1048.
Chem. Abst, vol. 115 #9 (1991) p. 768.

*Primary Examiner*—Yogendra N. Gupta
*Attorney, Agent, or Firm*—Kevin T. Mansfield

[57] ABSTRACT

Cationic compounds of formula wherein $R_1$ is the radical of formula

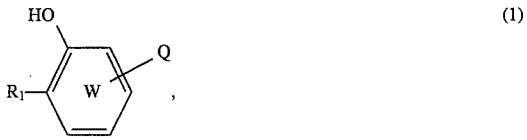

or

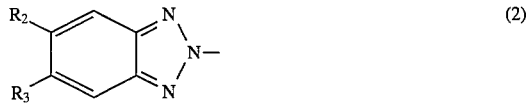

Q is a radical of formula

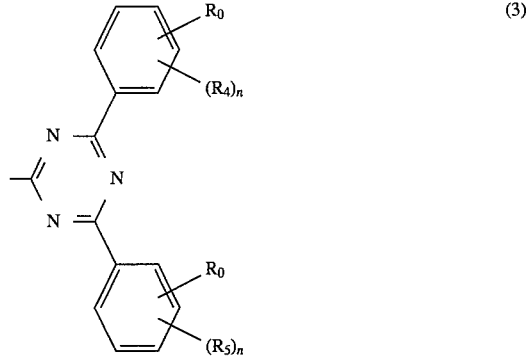

and the benzene ring W, in addition to being substituted by $R_1$, —OH and Q, may also be substituted by $C_1$–$C_6$alkyl and $C_1$–$C_4$alkoxy, and wherein $R_0$, $R_2$, $R_3$, $R_4$, $R_5$, $R_6$, n, $Y_1$, $Y_2$, $Y_3$ and $A^\ominus$ are as defined in claim 1, are suitable light stabilisers for photochemically stabilising basic dyeable polyamide fibre materials.

6 Claims, No Drawings

CATIONIC COMPOUNDS, THEIR PREPARATION AND THE USE THEREOF FOR THE PHOTOCHEMICAL STABILISATION OF BASIC DYEABLE POLYAMIDE FIBRE MATERIALS

The present invention relates to novel cationic compounds, to their preparation and to the use thereof for the photochemical stabilisation of basic dyeable polyamide fibre materials, as well as to the preparation of the novel starting materials required for the synthesis of the final products.

A substantial problem in the differential dyeing of carpets is the poor lightfastness of the basic dyeable polyamide component, especially the greening of the red component.

It has now been found that this problem can be largely solved by dyeing the fibre materials with dye liquors that additionally contain novel cationic compounds.

Accordingly, the present invention relates to novel cationic compounds of formula

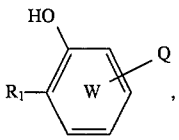  (1)

wherein $R_1$ is the radical of formula

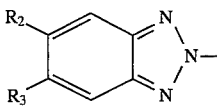  (2)

or

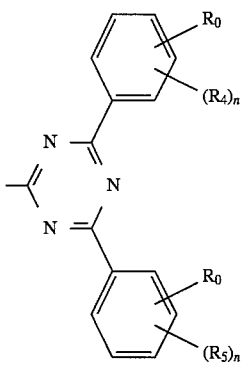  (3)

Q is a radical of formula

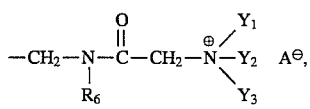  (4)

and the benzene ring W, in addition to being substituted by $R_1$, —OH and Q, may also be substituted by $C_1$–$C_6$alkyl and $C_1$–$C_4$alkoxy, and wherein $R_0$ is hydrogen or hydroxy, $R_2$ is hydrogen, halogen, $C_1$–$C_4$alkyl, $C_1$–$C_4$alkoxy, $C_2$–$C_9$alkoxycarbonyl or carboxy, $R_3$ is hydrogen or halogen, $R_4$ and $R_5$ are each independently of the other hydrogen, $C_1$–$C_4$alkyl, $C_1$–$C_4$alkoxy or halogen, or, when $R_0$ is hydroxy and n is 1, are also the group of formula Q, $R_6$ is hydrogen or $C_1$–$C_4$alkyl, and n is 1 or 2, $Y_1$ is unsubstituted $C_1$–$C_4$alkyl or $C_1$–$C_4$alkyl which is substituted by halogen, cyano, hydroxy or $C_1$–$C_4$alkoxy, or, together with $Y_2$ and the linking N-atom, forms a 5- to 7-membered heterocyclic ring, $Y_2$ is unsubstituted $C_1$–$C_4$alkyl or $C_1$–$C_4$alkyl which is substituted by halogen, cyano, hydroxy or $C_1$–$C_4$alkoxy, or, together with $Y_1$ and the linking N-atom, forms a 5- to 7-membered heterocyclic ring, $Y_3$ is hydrogen, unsubstituted $C_1$–$C_4$alkyl or $C_1$–$C_4$alkyl which is substituted by cyano, hydroxy, $C_1$–$C_4$alkoxy, phenyl or $C_1$–$C_4$alkoxycarbonyl, or is $C_3$–$C_4$alkenyl, or $Y_1$, $Y_2$ and $Y_3$, together with the linking N-atom, form an unsubstituted or a $C_1$–$C_4$alkyl-substituted pyridinyl or quinolinyl radical, and $A^{\ominus}$ is a colourless anion.

When n is 1 and $R_0$ is hydroxy, then the hydroxyl group is in 2-position and the group Q is in 4-position. $R_0$ is preferably hydrogen.

A 5- to 7-membered heterocyclic ring —$NY_1Y_2$ may suitably be a morpholino, piperidino, pyrrolidino or hexamethyleneimino ring (=hexahydro-1H-azepine).

A 5- to 7-membered heterocyclic ring —$NY_1Y_2Y_3$ may suitably be a pyridino, picolino, preferably α-picolino, or quinolino ring.

$Y_1$, $Y_2$ and $Y_3$ are preferably unsubstituted or hydroxy-substituted $C_1$–$C_4$alkyl.

Particularly interesting compounds are those of formula

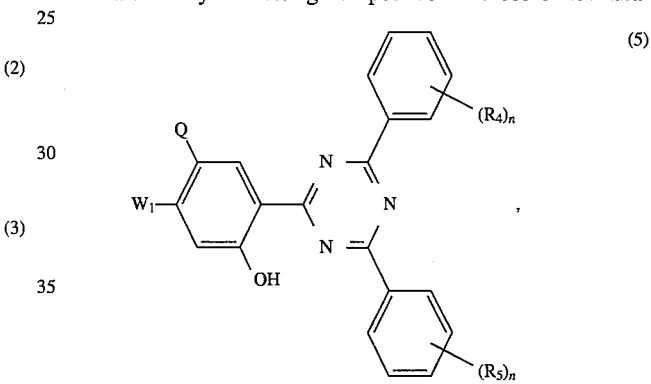  (5)

wherein $R_4$ and $R_5$ are hydrogen or $C_1$–$C_4$alkyl, Q and n are as defined for formula (1), and $W_1$ is $C_1$–$C_4$alkoxy, preferably methoxy.

Very particularly interesting compounds are those of formula

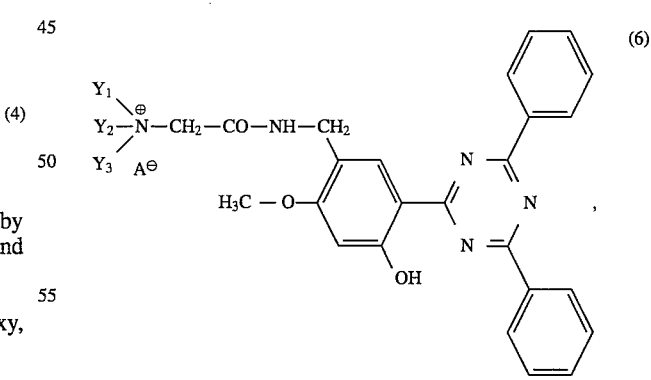  (6)

wherein $Y_1$ and $Y_2$ are each independently of the other methyl, ethyl or hydroxyethyl, and $Y_3$ is hydrogen, methyl or ethyl, or wherein $Y_1$ and $Y_2$, together with the linking nitrogen atom, are the morpholino radical, and $Y_3$ is hydrogen or methyl, or wherein $Y_1$, $Y_2$ and $Y_3$, together with the linking nitrogen atom, are pyridinyl, methyl-substituted pyridinyl, preferably α-picolinyl or quinolinyl, and $A^{\ominus}$ is $Cl^{\ominus}$, $CH_3SO_4^{\ominus}$ or $CH_3CO_2^{\ominus}$.

Other compounds of special interest are those of formula

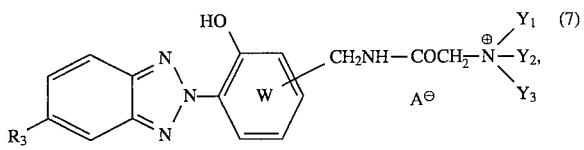 (7)

wherein $Y_1$ and $Y_2$ are each independently of the other methyl, ethyl or hydroxyethyl, and $Y_3$ is hydrogen, methyl or ethyl, or wherein $Y_1$ and $Y_2$, together with the linking nitrogen atom, are the morpholino radical, and $Y_3$ is hydrogen or methyl, or wherein $Y_1$, $Y_2$ and $Y_3$, together with the linking nitrogen atom, are pyridinyl, methyl-substituted pyridinyl, preferably α-picolinyl or quinolinyl, $R_3$ is hydrogen or chloro, $A^\ominus$ is $Cl^\ominus$, $CH_3SO_4^\ominus$ or $CH_3CO_2^\ominus$, and the benzene ring W is substituted by one or two $C_1$–$C_4$alkyl groups, preferably methyl and tert-butyl.

The substituents in the above formulae have the following meanings:

Halogen is fluoro, bromo and, preferably, chloro.

$C_1$–$C_4$Alkyl is methyl, ethyl, n-propyl, isopropyl, n-butyl, isobutyl, sec-butyl or tert-butyl.

$C_1$–$C_4$Alkoxy is methoxy, ethoxy, n-propoxy, isopropoxy, n-butoxy, isobutoxy, sec-butoxy or tert-butoxy.

$C_2$–$C_9$Alkoxycarbonyl is methoxycarbonyl, ethoxycarbonyl, n-propoxycarbonyl, n-butoxycarbonyl, pentoxycarbonyl, hexyloxycarbonyl, heptoxycarbonyl or octyloxycarbonyl.

The novel cationic compounds of formula (1) are prepared as follows:

a) to prepare compounds of formula (1), wherein $Y_1$, $Y_2$ and $Y_3$ are an unsubstituted or a $C_1$–$C_4$alkyl-substituted pyridinyl or quinolinyl radical, 1 molar equivalent of a compound of formula

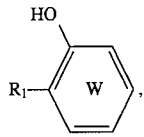 (8)

wherein $R_1$ and W are as defined for formula (1), is reacted with at least 1 molar equivalent of a compound that introduces the radical of formula

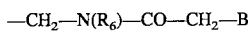 (9)

wherein

B is a leaving group such as chloro, and $R_6$ is as defined for formula (4), and subsequently the resultant compound of formula

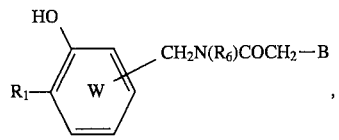 (10)

wherein $R_1$, $R_6$, B and W have the given meanings, is reacted with a compound that introduces the radical of formula

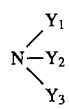 (11)

wherein $Y_1$, $Y_2$ and $Y_3$, together with the linking nitrogen atom, are an unsubstituted or a $C_1$–$C_4$alkyl-substituted pyridino or quinolino ring; or b) to prepare compounds of formula (1), wherein $Y_1$, $Y_2$ and $Y_3$ have a meaning that does not fall within process step a), 1 molar equivalent of a compound of formula

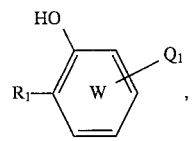 (12)

wherein $R_1$ and W are as defined for formula (1), and $Q_1$ is the radical of formula

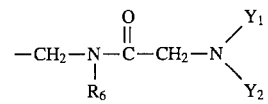 (13)

wherein $R_6$, $Y_1$ and $Y_2$ are as defined for formula (4), is quaternated or protonated with at least 1 molar equivalent of a compound of formula $$Y_3—A \qquad (14),$$

wherein $Y_3$ and A are as defined for formula (4), in the temperature range from 0° to 180° C.

The quaternisation or protonation is conveniently carded out in the temperature range from 30° to 140° C.

Suitable quaternising or protonating agents $Y_3$—A are typically: alkyl halides, including methyl iodide, ethyl iodide, ethyl bromide, butyl bromide or benzyl chloride; dialkyl sulfates such as dimethyl or diethyl sulfate; sulfonates such as methyl or ethyl tosylate or methyl or ethyl benzenesulfonate; alkylene oxides such as ethylene or propylene oxide or epichlorohydrin; acrylates such as methyl, ethyl or butyl acrylate, acrylonitrile; the compounds of formula

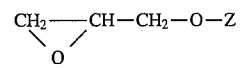

wherein Z is methyl, ethyl, propyl, butyl or phenyl; phosphites or phosphonates of formula

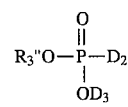

wherein $R_3''$ is alkyl of 1 to 4 carbon atoms, $D_2$ is hydrogen or unsubstituted alkyl or alkyl which is substituted by hydroxy, cyano, alkylcarbonyloxy or alkoxycarbonyl, each containing 1 to 4 carbon atoms in the alkyl moiety, and $D_3$ is alkyl of 1 to 4 carbon atoms.

The quaternisation of the compounds of formula (12) with alkyl halides, dialkyl sulfates or sulfonates to the compounds of formula (1) is conveniently carried out in a solvent that is inert to the alkylating agent. Typical examples of suitable solvents are hydrocarbons such as benzene, toluene and xylene; halogenated aliphatic or aromatic hydrocarbons, including chloroform, ethylene chloride, chlorobenzene and dichlorobenzene; alcohols, including ethanol, butanol, ethylene glycol and ethylene glycol monomethyl ether; ethers such as ethylene glycol dimethylether and dioxane; or amides such as dimethyl formamide and N-methylpyrrolidone.

The quaternisation with the cited alkylating agents is conveniently carded out in the temperature range from 0° to 180° C., preferably from 30° to 140° C.

The quaternisation of the compounds of formula (12) to the compounds of formula (1) with alkylene oxides, epichlorohydrin and derivatives thereof of formula

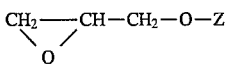

in which Z has the given meanings, acrylates or acrylonitrile, is carried out in the stated temperature ranges in acidic medium, conveniently in the presence of an organic acid such as formic acid, acetic acid, propionic acid or benzoic acid. It is, however, also possible to use inorganic acids such as sulfuric acid, phosphoric acid or hydrohalic acids for the quaternisation. These inorganic acids can be used in concentrated commercially available form, as dilute solutions or in admixture with the cited organic solvents, with or without the addition of water. When carrying out the reaction in the presence of an organic acid, the concentrated form of this acid will normally be used, by itself or in admixture with the cited organic solvents.

Illustrative examples of preferred phosphites and phosphonates are dimethyl phosphite, diethyl phosphite, dimethyl methanephosphonate, diethyl methanephosphonate, methyl ethylmethanephosphonate, methyl propylmethanephosphonate, methyl butylmethanephosphonate, methyl hexylmethanephosphonate, methyl octylmethanephosphonate, methyl decylmethanephosphonate, methyl dodecylmethanephosphate, dimethyl β-hydroxyethanephosphonate, dimethyl β-acetoxyethanephosphonate, dimethyl β-methoxycarbonylethanephosphonate and dimethyl β-cyanoethanephosphonate.

The reaction is carried out in water and/or an organic solvent such as methanol, ethanol, propanol, isopropanol, butanol, glycol, glycol methyl ether, glycol dimethyl ether, glycol butyl ether, diglycol methyl ether, methyl ethyl ketone, methyl butyl ketone, dimethyl formamide, sulfolane, oxypropionitrile, toluene, xylene, benzyl alcohol, phenoxyethanol, benzyloxypropionitrile, in the preferred temperature range from 60° to 190° C. When using liquid phosphites or phosphonates, the reaction can also be carried out in the absence of an additional solvent.

If it is desired to obtain protonated compounds of formula (1), i.e. acid addition salts thereof, then it is preferred to use mineral acids as protonating agents. Suitable protonating agents are quite generally all strong to medium strong organic acids or mineral acids.

Suitable solvents in which the protonation can be carried out are ordinarily all inert solvents. Preferred solvents are those in which the starting material dissolves and from which the final product precipitates immediately. Illustrative examples of such solvents are: aromatic hydrocarbons such as benzene, toluene and xylene; halogenated hydrocarbons, including trichloroethane, tetrachloroethylene, chlorobenzene or dichlorobenzene; and also nitro compounds such as nitromethane, nitropropane, nitrobenzene; alkanols and open-chain or cyclic ethers such as butanol, dibutyl ether, ethylene glycol, ethylene glycol monomethyl ether, ethylene glycol monoethyl ether, anisole or dioxane; ketones such as cyclohexanone or methyl ethyl ketone; fatty acid amides such as dimethyl formamide or dimethyl acetamide; sulfoxides such as dimethyl sulfoxide; and carboxylates such as ethyl acetate or butyl acetate.

The compounds of formula (8) are known and can be prepared by methods analogous to those for obtaining known compounds.

The compounds that introduce the radical of formula (9) are likewise known and can be prepared by methods analogous to those for obtaining known compounds. A typical example of a compound of formula (9) is N-hydroxymethylchloroacetamide.

The compounds of formula (10) are novel and constitute a further object of the invention.

The compounds of formula (11) are known. Typical examples are: pyridine, picoline, preferably α-picoline, and quinoline.

The compounds of formula (12) are also novel and therefore constitute a further object of the invention.

The compounds of formula (12) can be prepared by reacting a compound of formula

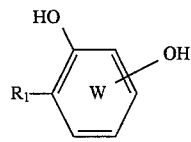 (15)

wherein $R_1$ and W have the given meanings, with a compound of formula

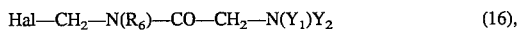

wherein Hal is chloro or bromo, and $R_6$, $Y_1$ and $Y_2$ are as defined for formula (4), in the presence of a base, preferably sodium or potassium hydroxide.

The compounds of formulae (15) and (16) are known and can be prepared by methods analogous to those for obtaining known compounds.

The reaction is carried out in the temperature range from 60° to 120° C., preferably from 30° to 60° C.

The compounds of formula (12) can, however, also be prepared by reacting a compound of formula

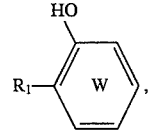 (17)

wherein $R_1$ and W have the given meanings,
a) with a compound of formula

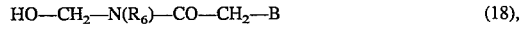

wherein B is a leaving group, preferably chloro or bromo, and $R_6$ is as defined for formula (4), and
b) reacting the resulting compound of formula

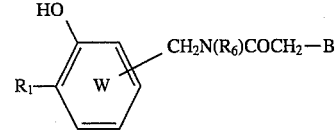 (10)

wherein $R_1$, $R_6$, W and B are as defined above, with a secondary or tertiary amine of formula

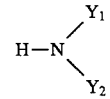 (19)

or

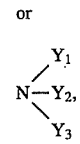 (20)

wherein $Y_1$, $Y_2$ and $Y_3$ are as defined for formula (4).

The compounds of formulae (17), (18), (19) and (20) are known and can be prepared by methods analogous to those for obtaining known compounds.

The first step a) is carried out in the temperature range from 60° to 120° C., and the second step b) in the temperature range from 20° to 180° C.

Accordingly, the invention also relates to the processes for the preparation of compounds of formulae (10) and (12).

The cationic light stabilisers of this invention are used for dyeing basic dyeable (acid-modified) polyamide fibre materials in order to stabilise the dyed fabrics against photochemical decomposition and to enhance the lightfastness of the dyeings.

The fibre materials which can be dyed in the presence of the novel light stabilisers are planar and, in particular, are floor coverings such as carpets. In addition to the above mentioned acid-modified fibre materials, they can consist of mixtures of unmodified (basic) and acid-modified polyamide materials. These materials are also known as differential dyeing polyamides and are described, inter alia, in W. Loy, Chemiefaserstoffe, Schiele und Schön, Berlin, 1978, pp. 132–141.

The invention thus also relates to a process for stabilising basic dye able polyamide fibre materials. The process comprises treating said fibre materials with a dye liquor which, in addition to containing a disperse dye or cationic dye, further contains a compound of formula (1).

The cationic dyes suitable for the process of this invention may belong to different dyestuff classes. They are preferably the customary salts, typically chlorides, sulfates or metal halides such as zinc chloride double salts of cationic dyes which may derive their cationic character from a carbonium, oxonium, sulfonium or, preferably, ammonium group. Illustrative examples of such chromophoric systems are azo dyes, especially monoazo or hydrazone dyes, diphenylmethane dyes, triphenylmethane dyes, methine or azomethine dyes, coumarin, ketoimine, cyanine, azine, xanthene, oxazine or thiazine dyes. Finally, it is also possible to use dye salts of the anthraquinone series containing an external onium group, typically an alkylammonium or cycloammonium group, as well as benzo,1-2-pyran dye salts that contain the cycloammonium group. The eligible disperse dyes, which are only very sparingly soluble in water and are substantially present in the dye liquor in the form of a fine dispersion, may belong to a very wide range of dyestuff classes, typically to the acridone, azo, anthraquinone, coumarin, methine, perinone, naphthoquinone, quinophthalone, styryl or nitro dyes.

Mixtures of cationic or disperse dyes may also be used in the process of this invention.

The invention further relates to a process for stabilising mixtures of acid and basic dyeable polyamide fibre materials. This process comprises treating said fibre materials with a liquor which, in addition to containing a cationic dye and a compound of formula (1), further contains an acid dye.

The acid dyes are typically salts of metal-free monoazo, disazo or polyazo dyes, including formazan dyes, as well as anthraquinone, xanthene, nitro, triphenylmethane and naphthoquinone-imine dyes. The acidic character of these dyes is determined by acid salt-forming substituents such as carboxylic acid groups, sulfuric acid groups and phosphonate groups, phosphonic acid groups or sulfonic acid groups. These dyes may also contain in the molecule reactive groupings that form a covalent bond with the material to be dyed. Acid dyes that contain a single sulfonic acid group are preferred.

Mixtures of these acid dyes may also be used, conveniently mixtures of at least two or three acid dyes.

The dyeing temperature is not lower than 70° C. and will usually be not higher than 106° C. The preferred temperature range is from 80° to 130° C.

The amount of dye will depend on the desired depth of shade. Usually amounts of 0.001 to 10 percent by weight, preferably from 0.01 to 5 percent by weight, based on the fibre material, have been found suitable.

Suitable fibre material is synthetic acid-modified polyamide, by itself or also in blends. Synthetic acid-modified polyamide is typically that obtained from adipic acid and hexamethylenediamine (polyamide 66), ε-caprolactam (polyamide 6), from ω-aminoundecanoic acid (polyamide 11), from ω-aminoenanthic acid (polyamide 7), from ω-aminopelargonic acid (polyamide 8) or from sebacic acid and hexamethylenediamine (polyamide 610) which has been modified with carboxylic acids or sulfocarboxylic acids.

The liquors suitable for use in the practice of this invention conveniently contain mineral acids, typically sulfuric acid or phosphoric acid, or organic acids such as formic acid, acetic acid, oxalic acid or, preferably, citric acid. They may also contain salts such as ammonium acetate, ammonium sulfate or sodium acetate. The acids are added in particular to adjust the pH of the formulations or liquors. The pH is usually in the range from 3 to 7, preferably from 3.5 to 4.5.

In addition to the light stabilisers, the dyes or fluorescent whitening agents, the concurrent use of other assistants conventionally employed in dyeing technology is also possible, including typically dispersants, levelling agents, electrolytes, wetting agents, antifoams, foam inhibitors or thickeners.

The liquors eligible for use in the practice of this invention may further contain photochemically active antioxidants such as copper complexes of bisazomethines. These copper complexes are disclosed, inter alia, in U.S. Pat. No. 4,655,783.

The invention is illustrated by the following Examples in which parts and percentages are by weight.

EXAMPLE 1

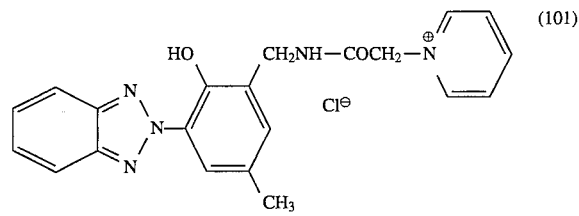

135 g of the compound of formula

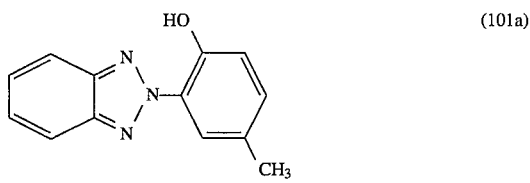

and 116 g of N-hydroxymethylchloroacetamide are homogenised and then added, with stirring, over 90 minutes at 0°–5° C. to 660 ml of sulfuric acid (95–97%). The reaction is allowed to go to completion for 2 hours at 0°–5°. The viscous, yellow solution is then poured over 20 minutes into 3000 g of a mixture of ice/water of 0°–5°. The resultant pale yellow suspension is stirred for 30 minutes, filtered, and the filter product is washed with water until neutral and then dried, giving 191 g (96.5% of theory) of the compound of formula

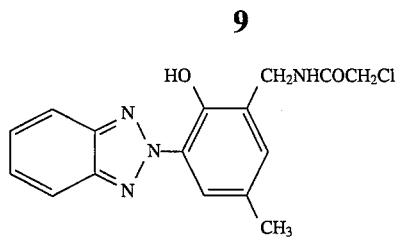

16.5 g of the compound of formula (101b) are heated to reflux in 85 ml of pyridine, whereupon the dense, white suspension goes into solution. After 3 minutes, crystals of the product precipitates. The suspension is stirred for 10 minutes, filtered, and the filter product is washed with toluene. The residue is dried at 90° C., giving 19.0 g (93% of theory) of the compound of formula (101).

The procedure described in this Example is repeated, but replacing pyridine with an equimolar amount of methyl pyridine, trimethylamine, diethyl methylamine, dimethyl β-hydroxyethylamine, morpholine, diethyl amine, dimethyl amine or quinoline, and using as compound of formula (101a) an equimolar amount of the compound of formula

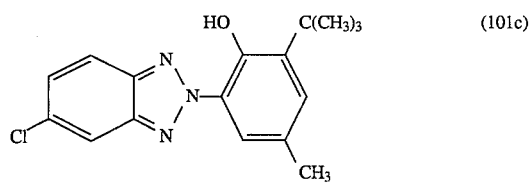

or

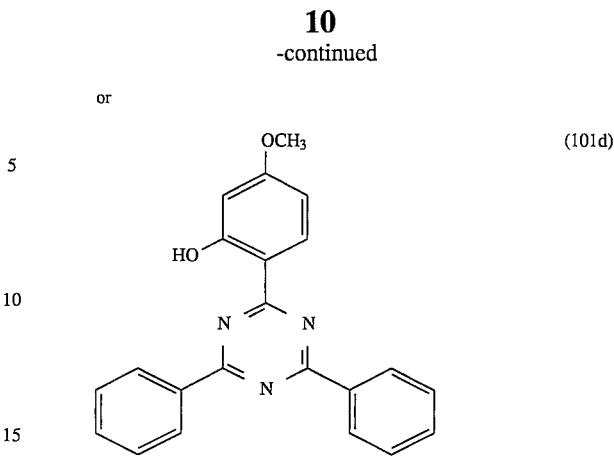

to give the compounds listed in the following Table. These compounds can also be prepared by reacting the compound of formula (101b) with a corresponding amine, and subsequently quaternising or protonating as described above.

TABLE 1

| Example | Compound of formula |
|---------|---------------------|
| 2 | ![structure] |
| 3 | ![structure] |
| 4 | ![structure] |
| 5 | ![structure] |

TABLE 1-continued
| Example | Compound of formula |
|---|---|
| 6 | 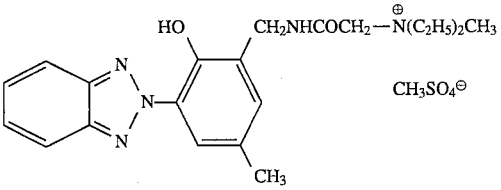 |
| 7 | 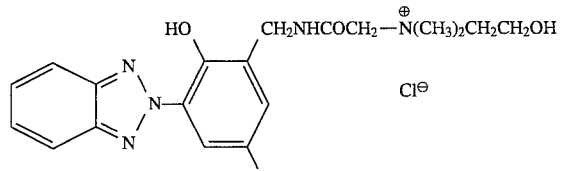 |
| 8 | 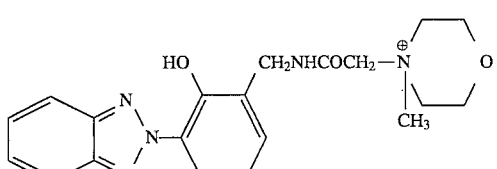 |
| 9 | 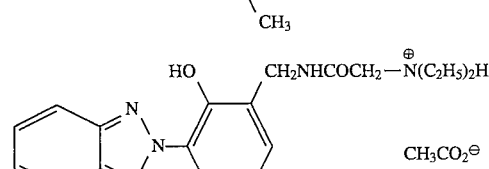 |
| 10 | 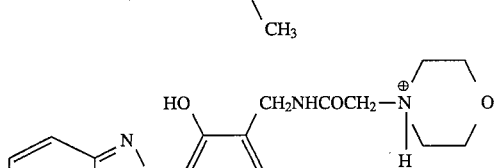 |
| 11 | 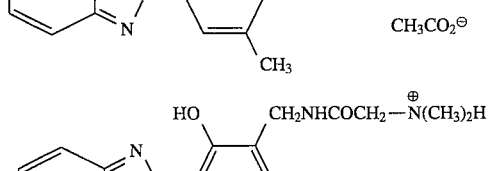 |
| 12 | 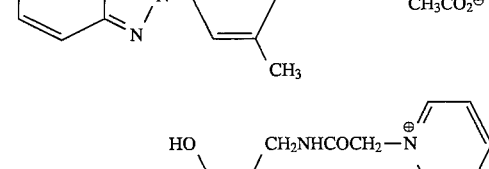 |

TABLE 1-continued
| Example | Compound of formula |
|---|---|
| 13 | 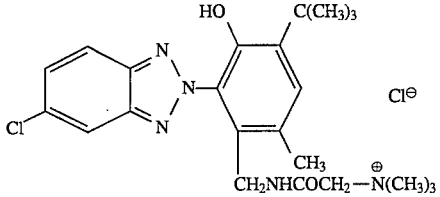 |
| 14 | 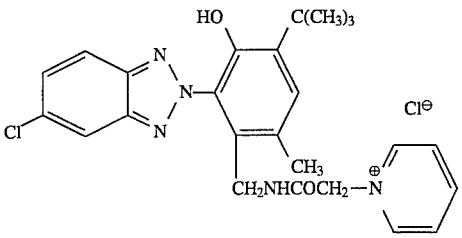 |
| 15 | 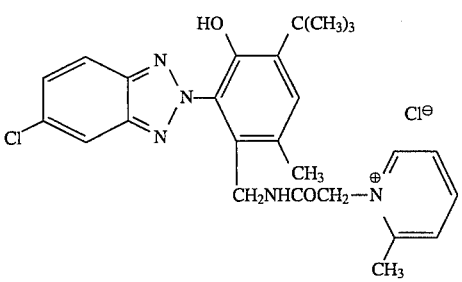 |
| 16 | 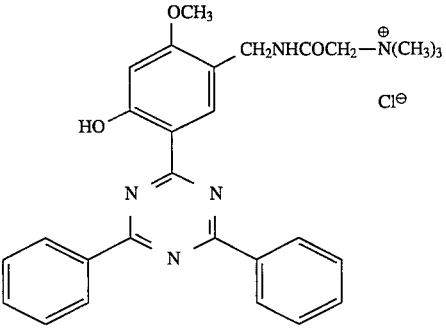 |
| 17 | 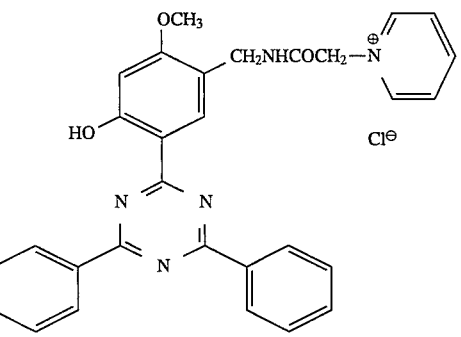 |

TABLE 1-continued

| Example | Compound of formula |
|---------|---------------------|
| 18 | (structure: benzene ring with OCH₃, OH, CH₂NHCOCH₂–N⁺(pyridine-CH₃), and triazine with two phenyl groups, Cl⁻) |

EXAMPLE 19

Four 10 g hanks of basic-modified polyamide (DUPONT 554F) are each treated in a dyeing machine (AHIBA® dyeing machine) with liquors (liquor to goods ratio 1:50) that have been adjusted to pH 4.5 with acetic acid and which contain the following dyes and ingredients (based on the fibre material): red-dyeing mixture comprising:

9 parts of the dye of formula (structure with pyrazole, azo linkage, $^{\ominus}OSO_3CH_3$)

36 parts of the dye of formula (structure with thiadiazole azo dye, $^{\ominus}OSO_3CH_3$);

and 1% of a non-ionic levelling agent.

The first dye liquor (A) contains 0.25% of the above dye mixture. The second dye liquor (B) contains 0.25% of the above dye mixture and 0.5% of compound (101) according to Example 1.

The third dye liquor (C) contains 0.25% of the above dye mixture and 1% of compound (101) according to Example 1.

The fourth dye liquor (D) contains 0.25% of the above dye mixture and 2% of compound (101) according to Example 1.

The material to be dyed is put into each liquor of 40° C. prepared as described above, treated for 5 minutes, and the temperature is raised to 95° C. at a rate of 1.5° C./minute. Dyeing is carded out for 30 minutes at this temperature, then 1% of acetic acid (80%), diluted with water, is added, and dyeing is continued for a further 30 minutes. The liquor is then cooled and the dyeing is rinsed in cold water, centrifuged and dried at 80° C.

The lightfastness of the dyeings is thereafter determined by the xenon light method (Swiss Standard SN-ISO 105-B02; evaluation according to the blue scale from 1 to 8).

The results are summarised in the following Table I.

TABLE I

| Liquor | Lightfastness xenon light 300 h |
|--------|---------------------------------|
| A | –4 |
| B | 5 |
| C | 5+ |
| D | 5–6 |

What is claimed is:
1. A cationic compound of the formula

$$\text{HO} \quad \text{Q} \quad (1)$$
$$R_1-\text{W}$$

wherein $R_1$ is the radical of the formula (2) (structure showing triazine ring connected to two phenyl groups bearing $R_0$, $(R_4)_n$ and $R_0$, $(R_5)_n$)

$$-CH_2-N-\overset{O}{\underset{R_6}{C}}-CH_2-\overset{\oplus}{N}\diagdown\overset{Y_1}{\underset{Y_3}{Y_2}} \quad A^{\ominus}, \quad (3)$$

and the benzene ring W, in addition to being substituted by $R_1$, —OH and Q, is unsubstituted or is substituted by $C_1$–$C_6$alkyl or $C_1$–$C_4$alkoxy, and wherein $R_0$ is hydrogen or hydroxy, $R_2$ is hydrogen, halogen, $R_4$ and $R_5$ are each independently of the other hydrogen, $C_1$–$C_4$alkyl, $C_1$–$C_4$alkoxy or halogen, or, when $R_0$ is hydroxy and n is 1, are also the group of formula Q, $R_6$ is hydrogen or $C_1$–$C_4$alkyl, and n is 1 or 2; or, when $R_1$ is a radical of the formula (2), $Y_1$ is unsubstituted $C_1$–$C_4$alkyl or $C_1$–$C_4$alkyl which is substituted by halogen, cyano, hydroxy or $C_1$–$C_4$alkoxy, $Y_2$ is unsubstituted $C_1$–$C_4$alkyl or $C_1$–$C_4$alkyl which is substituted by halogen, cyano, hydroxy or $C_1$–$C_4$alkoxy, $Y_3$ is hydrogen, unsubstituted $C_1$–$C_4$alkyl or $C_1$–$C_4$alkyl which is substituted by cyano, hydroxy, $C_1$–$C_4$alkoxy, phenyl or $C_1$–$C_4$alkoxycarbonyl, or is $C_3$–$C_4$alkenyl, or $Y_1$ together with $Y_2$ and the linking N-atom, form a morpholino ring, and $Y_3$ is hydrogen, unsubstituted $C_1$–$C_4$alkyl or $C_1$–$C_4$alkyl which is substituted by cyano, hydroxy, $C_{1-4}$alkoxy, phenyl or $C_1$–$C_4$alkoxycarbonyl, is $C_3$–$C_4$alkenyl, or $Y_1$, $Y_2$ and $Y_3$, together with the linking N-atom, form an unsubstituted or a $C_1$–$C_4$alkyl-substituted pyridinyl or quinolinyl radical; or $A^\ominus$ is a colourless anion.

2. A compound of the formula

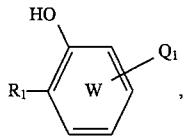

(12)

wherein $R_1$ is the radical of the formula

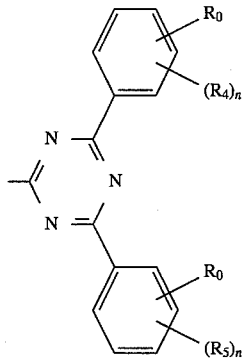

(3)

and $Q_1$ is the radical of the formula

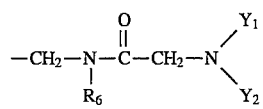

(13)

and the benzene ring W, in addition to being substituted by $R_1$, —OH and $Q_1$, is unsubstituted or substituted by $C_1$–$C_6$alkyl or $C_1$–$C_4$alkoxy, and wherein $R_0$ is hydrogen or hydroxy, $R_4$ and $R_5$ are each independently of the other hydrogen, $C_1$–$C_4$alkyl, $C_{1-4}$alkoxy or halogen, or, when $R_0$ is hydroxy and n is 1, are also a radical of the formula $Q_1$, $R_6$ is hydrogen or $C_1$–$C_4$alkyl, and n is 1 or 2, $Y_1$ is unsubstituted $C_1$–$C_4$alkyl or $C_1$–$C_4$alkyl which is substituted by halogen, cyano, hydroxy or $C_1$–$C_4$alkoxy, or, together with $Y_2$ and the linking N-atom, forms a morpholino ring or an unsubstituted or a $C_1$–$C_4$alkyl-substituted pyridinyl or quinolinyl radical, $Y_2$ is unsubstituted $C_1$–$C_4$alkyl or $C_1$–$C_4$alkyl which is substituted by halogen, cyano, hydroxy or $C_1$–$C_4$alkoxy, or, together with $Y_1$ and the linking N-atom, forms a morpholino ring an unsubstituted or a $C_1$–$C_4$alkyl-substituted pyridinyl or quinolinyl radical.

3. A compound according to claim 1, wherein a 5- to 7-membered heterocyclic ring —$NY_1Y_2Y_3$ is a pyridino, picolino or quinolino ring.

4. A compound according to claim 1 of the formula

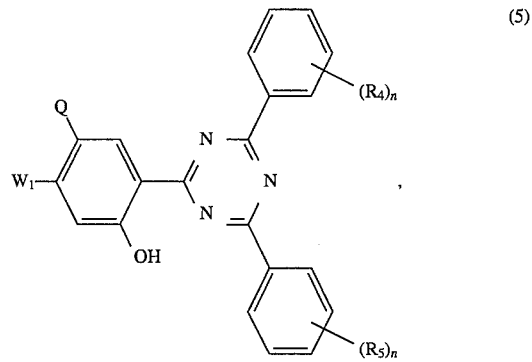

(5)

wherein $R_4$ and $R_5$ are hydrogen or $C_1C_4$alkyl, and $W_1$ is $C_1$–$C_4$alkoxy.

5. A compound according to claim 4, wherein $W_1$ is methoxy.

6. A compound according to claim 4 of the formula

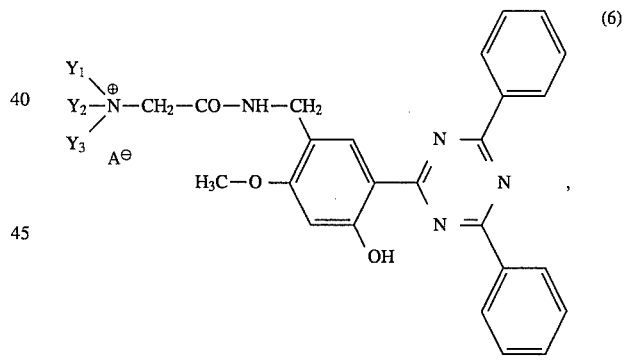

(6)

wherein $Y_1$ and $Y_2$ are each independently of the other methyl, ethyl or hydroxyethyl, and $Y_3$ is hydrogen, methyl or ethyl, or wherein $Y_1$ and $Y_2$, together with the linking nitrogen atom, are the morpholino radical, and $Y_3$ is hydrogen or methyl, or wherein $Y_1$, $Y_2$ and $Y_3$, together with the linking nitrogen atom, are pyridinyl, methyl-substituted pyridinyl, or quinolinyl, and $A^\ominus$ is a $Cl^\ominus$, $CH_3SO_4^\ominus$ or $CH_3CO_2^\ominus$ anion.

* * * * *